(12) United States Patent
Cao et al.

(10) Patent No.: US 7,927,799 B2
(45) Date of Patent: Apr. 19, 2011

(54) INHIBITORS OF PGHS-2 TRANSACTIVATOR ACTIVITY

(75) Inventors: Huiyu Cao, Cohoes, NY (US); Hung-Yun Lin, Schenectady, NY (US); Paul J. Davis, West Sand Lake, NY (US); Faith B. Davis, West Sand Lake, NY (US)

(73) Assignee: Ordway Research Institute, Albany, NY (US)

( * ) Notice: Subject to any disclaimer, the term of this patent is extended or adjusted under 35 U.S.C. 154(b) by 60 days.

(21) Appl. No.: 11/920,910

(22) PCT Filed: May 23, 2006

(86) PCT No.: PCT/US2006/019965
§ 371 (c)(1),
(2), (4) Date: May 7, 2009

(87) PCT Pub. No.: WO2006/127731
PCT Pub. Date: Nov. 30, 2006

(65) Prior Publication Data
US 2009/0298058 A1 Dec. 3, 2009

Related U.S. Application Data

(60) Provisional application No. 60/683,626, filed on May 23, 2005.

(51) Int. Cl.
*C12Q 1/68* (2006.01)
(52) U.S. Cl. ............... 435/6; 435/5; 435/7.1; 435/320.1
(58) Field of Classification Search ..................... None
See application file for complete search history.

(56) References Cited

FOREIGN PATENT DOCUMENTS

| EP | 1201766 | * | 5/2002 |
| EP | 1889057 | * | 4/2009 |
| WO | WO 98/37235 | * | 8/1998 |
| WO | WO98/37235 | * | 8/1998 |
| WO | WO2006/127731 | * | 11/2007 |

OTHER PUBLICATIONS

Wu et al. (Arteriosclerosis Thrombosis and Vascular Biology, vol. 25 No. 4, pp. 679-685, 2005).*
Liu et al. (Journal of Biological Chemistry, vol. 280, No. 5, pp. 3817-3823 Feb. 2005).*
Cao et al. (Am. J. Physiol., vol. 284, pp. C1429-1437, 2003).*
Arber et al, (1999), "Nonsteroidal anti-inflammatory drugs and prevention of colorectal cancer", Curr. Gastroenterol Rep, 1:441-448.*
Braunstein et al. (1996), "Efficient transcriptional silencing in *Saccharomyces cerevisiae* requires a heterochromatin histone acetylation pattern", Mol Cell Biol, 16:4349-4356.*
Cao et al. (1998), "Activation of human orbital fibroblasts through CD40 engagement results in a dramatic induction of hyaluronan synthesis and prostaglandin endoperoxide H synthase-2 expression. Insights into potential pathogenic mechanisms of thyroid-associated ophthalmopathy", J Biol Chem, 273:29615-29625.*
Cao et al. (1999), "Leukoregulin upregulation of prostaglandin endoperoxide H synthase-2 expression in human orbital fibroblasts", Am J Physiol, 277:C1075-1085.*
Cao et al. (2003), "Robust induction of PGHS-2 by IL-1 in orbital fibroblasts results from low levels of IL-1 receptor antagonist expression", Am J Physiol Cell Physiol, 284:1429-1437.*
Carey et al. (1983), "Antibodies to human squamous cell carcinoma", Otolarygnol Head and Neck Surg, 91:482-491.*
Davies (2003), "Cyclooxygenase-2 and chemoprevention of breast cancer", J Steroid Biochem Mol Biol, 86:495-499.*
Davies et al. (2002), "Cyclooxygenase-2 (COX-2), aromatase and breast cancer: a possible role for COX-2 inhibitors in breast cancer chemoprevention", Ann Onco, 113:669-678.*
Deng et al. (2003), "Quantitative analysis of binding of transcription factor complex to biotinylated DNA probe by a streptavidin-agarose pulldown assay", Analytical Biochemistry, 323(1):12-18.*
Smith et al. (2000), "Cyclooxygenases: structural, cellular, and molecular biology", Annu Rev Biochem, 69:145-182.*
Subbaramaiah et al. (2002), "Cyclooxygenase-2 is overexpressed in HER-2/neu-positive breast cancer: evidence for involvement of AP-1 and PEA3", J Biol Chem, 277:18649-18657.*
Wang et al. (1998), "Interleukin-1 beta and dexamethasone regulate gene expression of prostaglandin H synthase-2 via the NF-KB pathway in human amnion derived WISH cells", Prostaglandins Leokot Essent Fatty Acids, 59:63-69.*
Wang et al. (2004), "Cyclooxygenase-2: a potential target in breast cancer", Semin Oncol, 31(1 Suppl3):64-73.*
Wu et al. (2005), "Transcriptional control of COX-2 via C/EBPbeta", Arteriosclerosis, Thrombosis, and Vascular Biology, 25(4):679-685.*
Wulfing et al. (2004), "Cyclooxygenase-2 expression in bladder cancer: correlation with poor outcome after chemotherapy", Eur Urol, 45:46-52.*
Xiong et al. (2003), "Cyclooxygenase-2 expression and angiogenesis in colorectal cancer", World J Gastroenterol, 9:1237-1240.*
Xu et al. (1993), "Enhanced prostacyclin synthesis in endothelial cells by retovirus-mediated transfer of prostaglandin H synthase cDNA", J Clin Invest, 91:843-1849.*
Yoshimura et al. (2000), "Expression of cyclooxygenase-2 in prostate carcinoma", Cancer, 89-589-596.*
Yu et al. (2003), "Cyclooxygenase-2 expression in squamous dysplasia and squamous cell carcinoma of the esophagus", Cancer Lett, 198:193-201.*

(Continued)

*Primary Examiner* — Hope A Robinson
(74) *Attorney, Agent, or Firm* — Ivor R. Elrifi; Mintz, Levin, Cohn, Ferris, Glovsky and Popeo PC (57) ABSTRACT

Prostaglandin-endoperoxide H synthase (PGHS-2) converts arachidonic acid to prostaglandin $H_2$. PGHS-2 is an inducible gene product undetectable in most normal human tissues, but abundant in cancer cells. The present invention exploits a previously undisclosed transcriptional function of PGHS-2 distinct from its well-established enzymatic role to identify potential therapeutic agents useful in treating cancer. The method comprises a DNA binding assay in which PGHS-2 protein binding to the C/EBP, CRE and NF-κB regions of the PGHS-2 promoter in the presence and absence of test compounds is evaluated to identify inhibitors of PGHS-2 transactivation activity.

7 Claims, 8 Drawing Sheets

OTHER PUBLICATIONS

Zhu et al. (2002), "Dynamic regulation of cyclooxygenase-2 promoter activity by isoforms of CCAAT/enhancer-binding proteins", J Biol Chem, 277:6923-6928.*

Zimmermann et al. (1999), "Cyclooxygenase-2 expression in human esophageal carcinoma", Cancer Res, 59:198-204.*

Liu et al. (2005), "Cyclooxygenase-2 suppresses hyoxia-induced apoptosis via a combination of direct and indirect inhibition of p53 activity in a human prostate cancer cell line", Journal of Biological Chemistry, 280(5):3817-3823.*

Luo et al. (1998), "Rb interacts with histone deacetylase to repress transcription", Cell 92:463-473.*

Marvin et al. (2000), "Subcellular localization of prostaglandin R synthase-2 in a human amnion cell line: implications for nuclear localized prostaglandin signaling pathways", Prostaglandins Leukot Essent Fatty Acids, 62:7-11.*

Meade et al. (1999), "Perioxisome proliferators enhance cyclooxygenase-2 expression in epithelial cells", J Biol Chem, 274:8328-8334.*

Molina-Holgado, E. et al. (2000), "Induction of COX-2 and PGE(2) biosynthesis by IL-1 beta is mediated by PKC and mitogen-activated protein kinases in murine astrocytes", Br I Pharmacol, 131:152-159.*

Momand et al. (1992), "The mdm-2 oncogene product forms a complex with the p53 protein and inhibits p53-mediated transactivation", Cell, 69:1237-1245.*

Moran (2002), "Epidemiological and clinical aspects of nonsteroidal anti-inflammatory drugs and cancer risks", J Environ Pathol Toxicol Oncol, 21:193-201.*

Morita et al. (1995), "Expression-activity profiles of cells transfected with prostaglandin endoperoxide H synthase measured by quantitative fluorescence microscopy", Biochemistry, 34:7194-7199.*

Oshima et al. (1996), "Supression of intestinal polyposis in Apc delta716 knockout mice by inhibition of cyclooxygenase 2 (COX-2)", Cell, 87:803-809.*

Pai et al. (2002), "Prostaglandin E2 trans activates EGF receptor: a novel mechanism for promoting colon cancer growth and gastrointestinal hypertrophy", Nat Med, 8:289-293.*

Pang et al. (2002), "Protein kinase C-epsilon mediates bradykinin-induced cyclooxygenase-2 expression in human airway smooth muscle cells", Faseb J, 16:1435-1437.*

Parfenova et al. (2001), "Dynamics of nuclear localization sites for COX-2 in vascular endothelial cells", Am J Physiol Cell Physiol, 281:C166-178.*

Patel et al. (2002), Regulation of MDR-1 (P-glycoprotein) by cyclooxygenase-2, J Biol Chem, 277:38915-38920.*

Piazuelo et al. (2003), "COX-2 inhibition in esophagitis, Barrett's esophagus and esophageal cancer", Curr Pharm Des, 9:2267-228024.*

Potter et al. (2000), "NF-IL6 and CRE elements principally account for both basal and interleukin-1β-induced transcriptional activity of the proximal 528 bp of the PGHS-2 promoter in amnion-derived AV3 cells: evidence for involvement of C/EBPβ", Molecular Human Reproduction, 6(9):771-778.*

Robbins et al. (1993), "Regulation and properties of extracellular signal-regulated protein kinases 1 and 2 in vitro", J Biol Chem, 268:5097-5106.*

Rollins et al. (1980), "Subcellular localization of prostaglandin-forming cyclooxygenase in Swiss mouse 3T3 fibroblasts by electron microscopic immunocytochemistry", J Biol Chem, 255:4872-4875.*

Smith et al. (1981), "Subcellular localization of prostaglandin forming enzymes using conventional and monoclonal antibodies", Prog Lipid Res, 20:103-110.*

Smith et al. (1996), "Prostaglandin endoperoxide H synthases (cyclooxygenases)-1 and 2", J Biol Chem, 271:33157-33160.*

Smith et al. (1996), "Prostaglandin endoperoxide H synthases-1 and 2", Adv Immuno, 162:167-215.*

Deng et al. (2004), "Role of p300 and PCAF in regulating cyclooxygenase-2 promoter activation by inflammatory mediators", Blood, 103:2135-2142.*

Funk et al. (1991), "Human platelet/erythroleukemia cell prostaglandin GM synthase: cDNA cloning, expression, and gene chromoomal assignment", FASEB J, 5:2304-2312.*

Gately et al. (2004). "Multiple roles of COX-2 in tumor angiogenesis: a target for antiangiogenic therapy", Semin Oncol, 31:2-11.*

Goppelt-Struebe et al. (2000), "Induction of cyclooxygenase-2 by platelet-derived growth factor (PDGF) and its inhibition by dexamethasone are independent of NF-kappaB/IkappaB transcription factors", Naunyn Schmiedebergs Arch Pharmacol, 361:636-645.*

Guo et al. (2001), "Activator protein-1 transcription factor mediates bombesin-stimulated cyclooxygenase-2 expression in intestinal epithelial cells", J Biol Chem, 276:22941-22947.*

Habib et al. (1995), "Increased expression of inducible cyclooxygenase-2 in human endothelial cells by antiphospholipid antibodies", Thromb Haemost, 74:770-777.*

Han et al. (2002), "Up-regulation of prostaglandin E2 synthesis by interleukin-1 beta in human orbital fibroblasts involves coordinate induction of prostaglandinendoperoxide H synthase-2 and glutathione-dependent prostaglandin E2 synthase expression", J Biol Chem, 277:16355-16364.*

Hanahan et al. (2000), "The hallmarks of cancer", Cell, 100:57-70.*

Harrison et al. (2000), "Involvement of CCAAT Enhancer Binding Protein Transcription Factors in the Regulation of Prostaglandin G/H Synthase 2 Expression by Interleukin-1 in Osteoblastic MC3T3-E1 Cells", J of Bone and Mineral Research, 15(6):1138-1146.*

Hendrickx et al. (2003), "Up-regulation of cyclooxygenase-2 and apoptosis resistance by p38 MAPK in hypericin-mediated photodynamic therapy of human cancer cells", J Biol Chem, 278:52231-52239.*

Hoshino et al. (2003), "Prostaglandin E2 protects gastric mucosal cells from apoptosis via EP2 and EP4 receptor activation", J Biol Chem, 278:12752-12758.*

Howe et al. (2001), "Cyclooxygenase-2 : a target for the prevention and treatment of breast cancer", Endocr Relat Cancer, 8:97-114.*

Ishaque et al. (2003), "Cyclooxygenase-2 inhibits tumor necrosis factor alpha-mediated apoptosis in renal glomerular mesangial cells", J Biol Chem, 278:10629-10640.*

Jang et al. (1996), Activator protein 1 activity is involved in the regulation of the cell type-specific expression from the proximal promoter of the human profilaggrin gene, J Biol Chem, 271:24105-24114.*

Kujubu et al. (1993), "Expression of the protein in product of the prostaglandin synthase-2/TIS 10 gene in mitogen-stimulated Swiss 3T3 cells", J Biol Chem, 268:5425-5430.*

Lim et al. (2002), Expression of Ku70 and Ku80 mediated by NF-kappa B and cyclooxygenase-2 is related to proliferation of human gastric cancer cells, J Biol Chem, 277:46093-46100.*

Lin et al. (1999), "Thyroid hormone induces activation of mitogen-activated protein kinase in cultured cells", Am J Physiol, 276:C1014-1024.*

Lin et al. (2002), "Resveratrol induced serine phosphorylaytion of p53 causes apoptosis in a mutant p53 prostate cancer cell line", J Urol, 168:748-755.*

Liou et al. (2001), "Colocalization and interaction of cyclooxygenase-2 with caveolin-1 in human fibroblasts", J Biol Chem, 276:34975-34982.*

* cited by examiner

INHIBITORS OF PGHS-2 TRANSACTIVATOR ACTIVITY

RELATED APPLICATIONS

This application is a national stage application, filed under 35 U.S.C. §371, of International Application No. PCT/US2006/019965, filed on May 23, 2006 which claims the benefit of U.S. Ser. No. 60/683,626, filed May 23, 2005.

FIELD OF THE INVENTION

The present invention relates to inhibitors of PGHS-2 transactivation function and in particular to methods of screening for inhibitors of PGHS-2 transactivation.

BACKGROUND OF THE INVENTION

Prostaglandin-endoperoxide H synthase (PGHS) is a rate-limiting enzyme in the production of prostaglandins (Smith et al., 1996). PGHS catalyzes the cyclooxygenation of arachidonic acid to prostaglandin $G_2$ ($PGG_2$) and the reduction of $PGG_2$ to prostaglandin $H_2$ ($PGH_2$). $PGH_2$ is then metabolized by different synthases to variable function prostanoids, including prostaglandins $PGD_2$, $PGE_2$, $PGF_{2\alpha}$, and $PGI_2$, and thromboxane ($TXA_2$) (Smith and DeWitt, 1996). PGHS-1 and PGHS-2 are single copy genes that have been mapped to human chromosomes 9 and 1, respectively (Xu et al., 1993; Funk et al., 1991). PGHS-1 is constitutively expressed in most tissues (Smith et al., 2000). In contrast, PGHS-2 is an immediate-early response gene that is highly inducible in nonmalignant cells by cytokines and inflammatory stimuli (Cao et al., 2003; Cao and Smith, 1999; Cao et al., 1998). It is distinct from PGHS-1 with respect to DNA sequence, stability of its mRNA and responses to various stimuli.

In many cancer cell lines and cancer tissues, however, PGHS-2 is constitutively expressed (Davies et al., 2002). The importance of PGHS-2 to tumor cell biology has been attributed in part to the vascular endothelial growth factor (VEGF)-dependent angiogenic activities of $PGE_2$ and $PGI_2$ that support tumor growth (Gately and Li, 2004). Colocalization and interaction of PGHS-2 with caveolin-1, which is segregated from the general prostaglandin synthesis factory in endoplasmic reticulum and nuclear envelope, may contribute to tumorigenesis and to inflammation (Liou et al., 2001). $PGE_2$ can also inhibit apoptosis and immune surveillance (Hoshino et. al., 2003; Ishaque et al., 2003) and $PGE_2$ induces certain DNA repair proteins (Ku70 and Ku80) whose expression may be related to human gastric cancer cell proliferation and carcinogenesis (Lim et al., 2002).

PGHS-2 expression has been associated with less differentiated and more aggressive breast carcinomas and thus may be a useful tissue indicator of prognosis, as well as a target for drug therapy (Wulfing et al., 2004). PGHS-2 overexpression has been reported to occur in more than 40% of human invasive breast cancers and 60% of ductal carcinomas in situ (Wang and Dubois, 2004). Expression of multidrug-resistance gene 1 is increased when PGHS-2 is overexpressed experimentally, suggesting that PGHS-2 contributes to multidrug-resistance in tumors (Patel et al., 2002). In addition, Subbaramaiah et al. (2002) have shown that hyperexpression of PGHS-2 is associated with excessive expression of HER-2/neu in breast cancers through enhancement of the Ras signal.

SUMMARY OF THE INVENTION

We report here the presence of PGHS-2 protein, but not PGHS-1, in the cell nucleus of tumor cells and we show that PGHS-2 binds to the promoter region of its own gene and can function as a transactivator. We propose that this direct positive feedback mechanism contributes to constitutive expression of PGHS-2 in cancer cells. The present invention, therefore, provides a method of screening for selective inhibitors of the transactivator function of PGHS-2 which could then be used as therapeutic agents in the treatment of cancer, without the adverse side effects associated with inhibitors of PGHS-1.

In one aspect, therefore, the invention relates to a method for identifying inhibitors of constitutive PGHS-2 expression by inhibition of its transactivation activity, wherein the method comprises the steps of contacting a nucleic acid probe that corresponds to at least one region of the PGHS-2 or MDM2 promoter with PGHS-2 protein in the presence and absence of a test compound and determining the level of binding of PGHS-2 protein to the promoter. A decrease in the amount of protein bound in the presence of said test compound compared to the amount of protein bound in the absence of said test compound indicates that the compound is a potential inhibitor of PGHS-2 transactivation activity.

In one embodiment, the level of binding is determined by a DNA-protein binding assay, for example, a chromatin immunoprecipitation assay or an electrophoretic mobility shift assay (EMSA).

In one embodiment, the nucleic acid probe corresponds to one region of the PGHS-2 promoter: a c/EBP site, a CRE site or a NF-κB site and the probe is labeled.

In one embodiment, the nucleic acid probe is biotinylated and is incubated with streptavidin-coated beads so that nuclear extract proteins bound to the probe can be isolated and subsequently eluted from the beads.

In a related aspect, the present invention relates to a method of screening for PGHS-2 inhibitors, wherein the method comprises obtaining a cell that constitutively produces PGHS-2, wherein the cell has been transfected with a first nucleic acid corresponding to a region of the PGHS-2 promoter and a second nucleic acid encoding a reporter molecule; exposing the cell to a test compound; isolating a nuclear extract from the cell; and comparing the level of reporter molecule in said extract with the level of reporter molecule in a nuclear extract from unexposed cells, wherein a decrease in the level of reporter molecule is indicative of inhibition of PGHS-2 transactivation. The reporter molecule may be, for example, luciferase or green fluorescence protein.

BRIEF DESCRIPTION OF THE DRAWINGS

A: Immunofluorescent staining of PGHS-1 and PGHS-2 in ECV 304, prostate (DU145), and head and neck (UM-SCC-22B) cell lines. ECV 304, DU145 and UM-SCC-22B cells were subjected to indirect immunofluorescent staining using monoclonal antibody to human PGHS-I and PGHS-2 followed by Alexa-488-labeled goat anti-mouse antibody. Top 3 panels: antibody to PGHS-1; lower 3 panels: antibody to PGHS-2.

B: Subcellular localization of immunofluorescence staining for PGHS-1 and PGHS-2 in UM-SCC-22B cells. These cells, which constitutively express both PGHS-1 and PGHS-2, were subjected to indirect immunofluorescence staining (green) and nuclear staining with TO-PRO-3 iodide (red). Nuclear PGHS-2, but not PGHS-1, is demonstrated by superimposition of the PGHS-2 stain on the nuclear stain, creating a yellow-orange color.

FIG. 2. Expression of PGHS-2 in ECV 304, DU145 and UM-SCC-22B (22B) cells A: Constitutive expression of PGHS-2 protein in ECV 304, DU145 and UM-SCC-22B cells. Cells were grown to confluence in 10 cm dishes. Monolayers were treated with or without PMA (100 nM) for 12 h; nuclear proteins were then harvested and subjected to immunoblotting with antihuman PGHS-2 (panel 1) or -PGHS-1 (panel 2). The bar graph shows the changes from control in nuclear or cytosol band image intensities (mean:1:SD) with each treatment, from results of three experiments.

B: PGHS-2 mRNA levels in ECV 304, DU145 and UM-SCC-22B cells. Confluent cells were treated with or without PMA (100 nM) for 8 h. Total RNA samples were harvested and subjected to RT-PCR using PGHS-2 or GAPDH primers (top and bottom panels, respectively). The bar graph shows the increases in PGHS-2 mRNA levels relative to control samples (mean±SD) and corrected for changes in GAPDH in the same samples, summarized from results of three experiments.

A: Effects of PKC activation or signaling pathway inhibitors on PGHS-2 expression. UM-SCC 22B cells were allowed to grow to confluence in 10 cm culture dishes, and then received either control medium (lane 1) or medium containing PMA (lane 2, 100 nM), PD98059 (PD, lane 3, 10 μM), SB203580 (SB, lane 4, 10 μM) or PDTC (lane 5, 100 μM) for 16 h. Cell monolayers were harvested and 40 μg nuclear protein were subjected to immunoblotting with anti-human PGHS-2 (upper panel) or anti-pMAPK (pERK1/2, lower panel). The bar graph below shows the band intensities in control samples and in cells treated with the agents indicated. Results shown are the means±SD from three similar experiments.

B: Effect of dominant negative ERK1/2 transfection on PGHS-2 expression in UM-SCC-22B cells. Cells were transfected with dominant negative mutants of ERK1 (dnERK1), ERK2 (dnERK2), both mutants or empty vector (pCEP40). Nuclear preparations were analyzed by western blotting for PGHS-2 and pMAPK (phosphorylated ERKs 1 and 2).

Cells were plated in 48-well culture dishes and treated or without PMA (100 nM), NS398 (10 μM), indomethacin (10 μM) or PD98059 (10 μM) for 12 h. Cells were transferred to 200 μl PBS for the last 30 min. Samples were then collected and subjected to quantitative analysis of $PGE_2$ by ELISA. The results are shown as mean±SD of results from three representative studies.

Confluent UM-SCC-22B (22B) cells were treated with PMA, 100 nM, or solvent alone for 12 h. Cell nuclei were prepared (Lin et al., 1999) and immunoprecipitated with antibody to PGHS-2. Immunoprecipitated proteins were separated by gel electrophoresis and immunoblotted with antibody to c-Fos, MDM2 or p300. Shown are representative immunoblots from 3 similar experiments. Co-localization of c-Fos with PGHS-2 is seen in nuclei of UM-SCC-22B cells.

Aliquots of cells were treated with PMA (100 mM), PD98059 (10 μM), PDTC (100 μM), or SB203580 (10 μM) for 12 h. Cultures were co-transfected with β-galactosidase reporter plasmids, and luciferase activity, corrected for β-galactosidase activity, measured and expressed as the mean±SD of triplicate culture determinations from three experiments.

B: Binding of PGHS-2 to PGHS-2-specific NF-κB (−213/−222; −438/−447), C/EBP (−132/−124) and CRE (−59/53) sequences. Confluent UM-SCC-22B (22B) cells were treated with or without PMA (100 nM) for 6 h and nuclear extracts were prepared. A biotinylated PGHS-2 promoter DNA probe was incubated with streptavidin-coated beads for 1 h; the pelleted beads were collected and washed, the proteins eluted and subjected to western blot analysis using anti-PGHS-2 antibody.

Eighty percent confluent 293T cells were transiently transfected with increasing concentrations of PGHS-2 expression vector in PCMV, or control vector, and the PGHS-2 promoter (−831/+123) fused to a luciferase reporter. PCMV β-Gal was transfected for control of transfectional efficiency. Luciferase activity was determined by a Dual-light system. The graph shows the change in luciferase activity relative to a control value of 1, obtained from data in 3 experiments.

DETAILED DESCRIPTION OF THE INVENTION

Subcellular Location of PGHS-1 and PGHS-2 in Cancer Cell Lines

Figure 1:
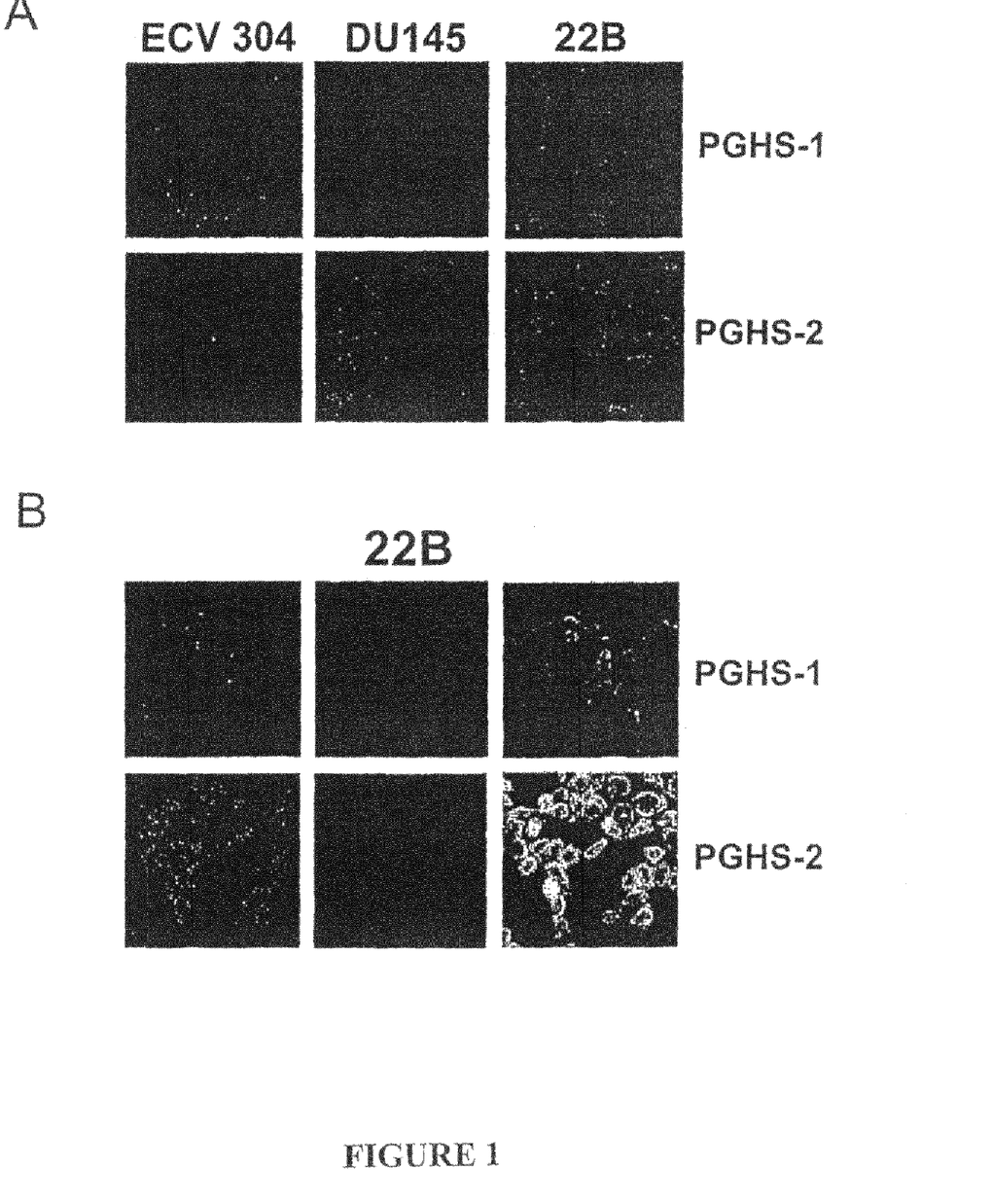
FIG. 1. Localization of PGHS-1 and PGHS-2 in DU145 and UM-SCC-22B (22B) cancer cell lines and ECV 304 endothelial cells.

Previous studies of subcellular localization of PGHS isoforms have shown that PGHS-1 and PGHS-2 are both found in the endoplasmic reticulum and at the nuclear envelope of fibroblasts and macrophages and that there is no substantial difference in the subcellular distribution of the two isozymes (Morita et al., 1995; Smith et al., 1981; Rollins et al., 1980; Kujubu et al., 1993). In the current studies, we compared the distributions of PGHS-1 and PGHS-2 in human prostate (DUI45) and head and neck (UM-SCC-22B) cancer cells. Shown in FIG. 1 are confocal photomicrographs of cancer cells stained by indirect immunofluorescence, using primary antibodies specific for either PGHS-1 or PGHS-2. PGHS-1 immunoreactivity was evenly distributed in peripheral cytoplasm. PGHS-1 is known to be present in the endoplasmic reticulum of many cells and it is likely that the fluorescent staining of PGHS-1 we observed largely reflects localization of the enzyme in endoplasmic reticulum.

In contrast to PGHS-1, PGHS-2 in cancer cells was concentrated at the nuclear envelope and was present in abundant quantities within the cell nucleus (FIG. 1). Results from the cancer cell lines were compared with those from endothelial cells (ECY 304). Only trace PGHS-2 immunoreactivity appeared in cytoplasm of ECY 304 cells and there was no PGHS-2 staining at the nuclear envelope or inside the nuclei of these cells. As shown in FIG. 1B, the fluorescence staining of PGHS-2 (green) overlaps with nuclear staining (red). On the other hand, the staining of PGHS-1 in UM-SCC-22B cells did not overlap with nuclear staining.

Figure 2:
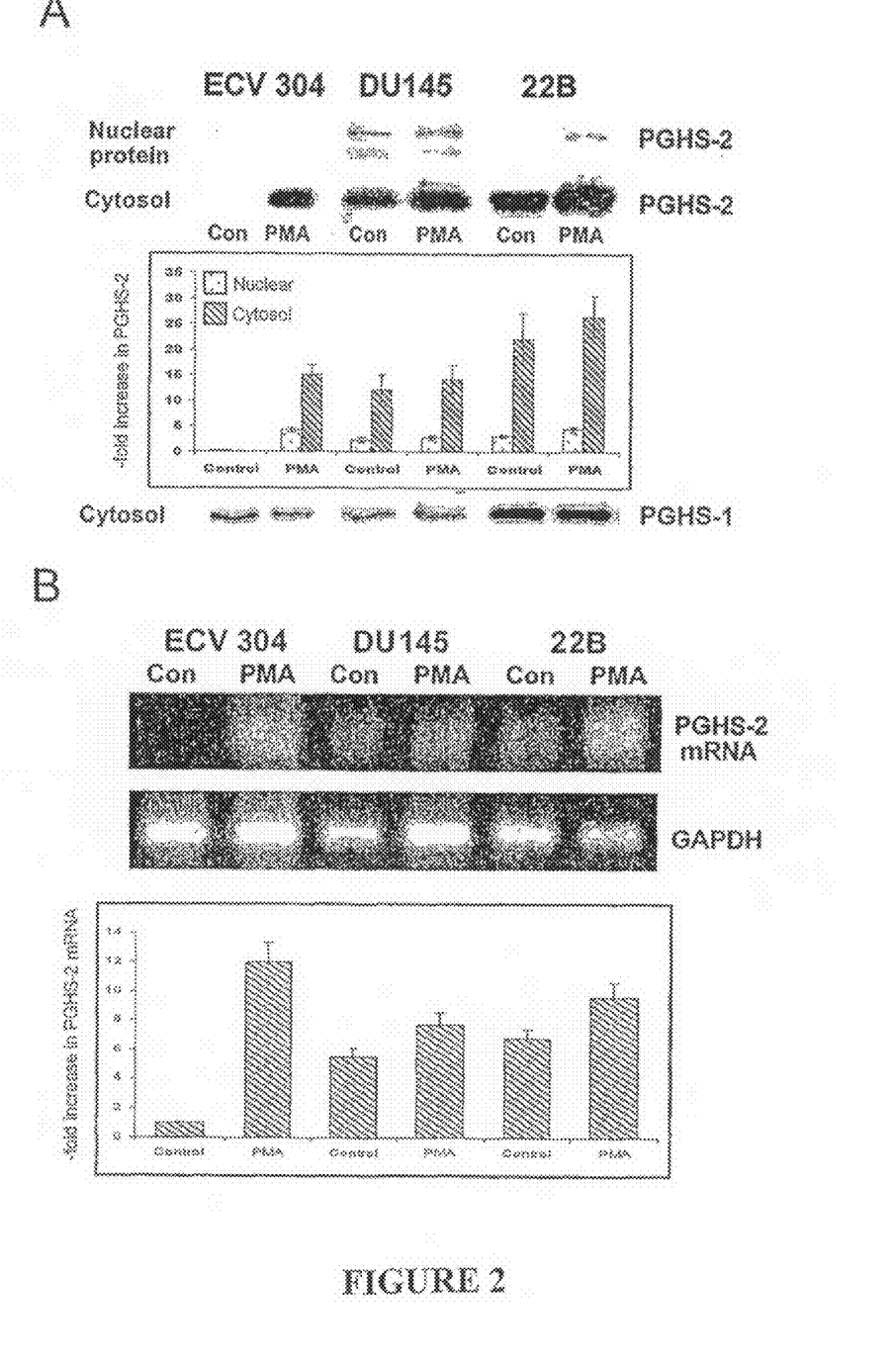

Relationship of High Levels of PGHS-2 Protein and mRNA in Cancer Cell Lines to Elevated NF-KB, MAPK (ERK1l2) and p38 Activity Western blots of nucleoproteins obtained by fractionation of DU145 and UM-SCC-22B cells showed that PGHS-2 protein was recovered in the nuclear fractions of these cells, more so in the UM-SCC-22B cells than in DU145 cells (FIG. 2A). PGHS-2 mRNA levels were also found to be readily detectable in DU145 and UM-SCC-22B cancer cells (FIG. 2B). PGHS-2 protein and mRNA levels were undetectable in untreated ECY 304 cells. It should be noted that these findings were made in cells unexposed to cytokines or growth factors that can influence cellular PGHS-2 levels and cause nuclear translocation of the enzyme (Liou et al., 2001). PGHS-1 protein was abundant in the head and neck cancer cells (UM-SCC-22B), as well as in DU145 prostate cancer and ECY 304 endothelial cells (FIG. 2A).

Phorbol-myristate acetate (PMA) in short-term studies activates protein kinase C (PKC) and rapidly induces PGHS-2 gene transcription (Pang et al., 2002). In the three cell lines studied here, abundance of PGHS-2 mRNA and of PGHS-2 protein in nuclei was increased by treatment of cells with PMA (FIGS. 2A and B), with most marked changes seen in the UM-SCC-22B cells. Cytosolic PGHS-2 also increased with PMA treatment (FIG. 2A). As expected, incubation of cancer cell lines with PMA (100 nM) for 12 h had no effect on abundance of PGHS-1.

Figure 3:
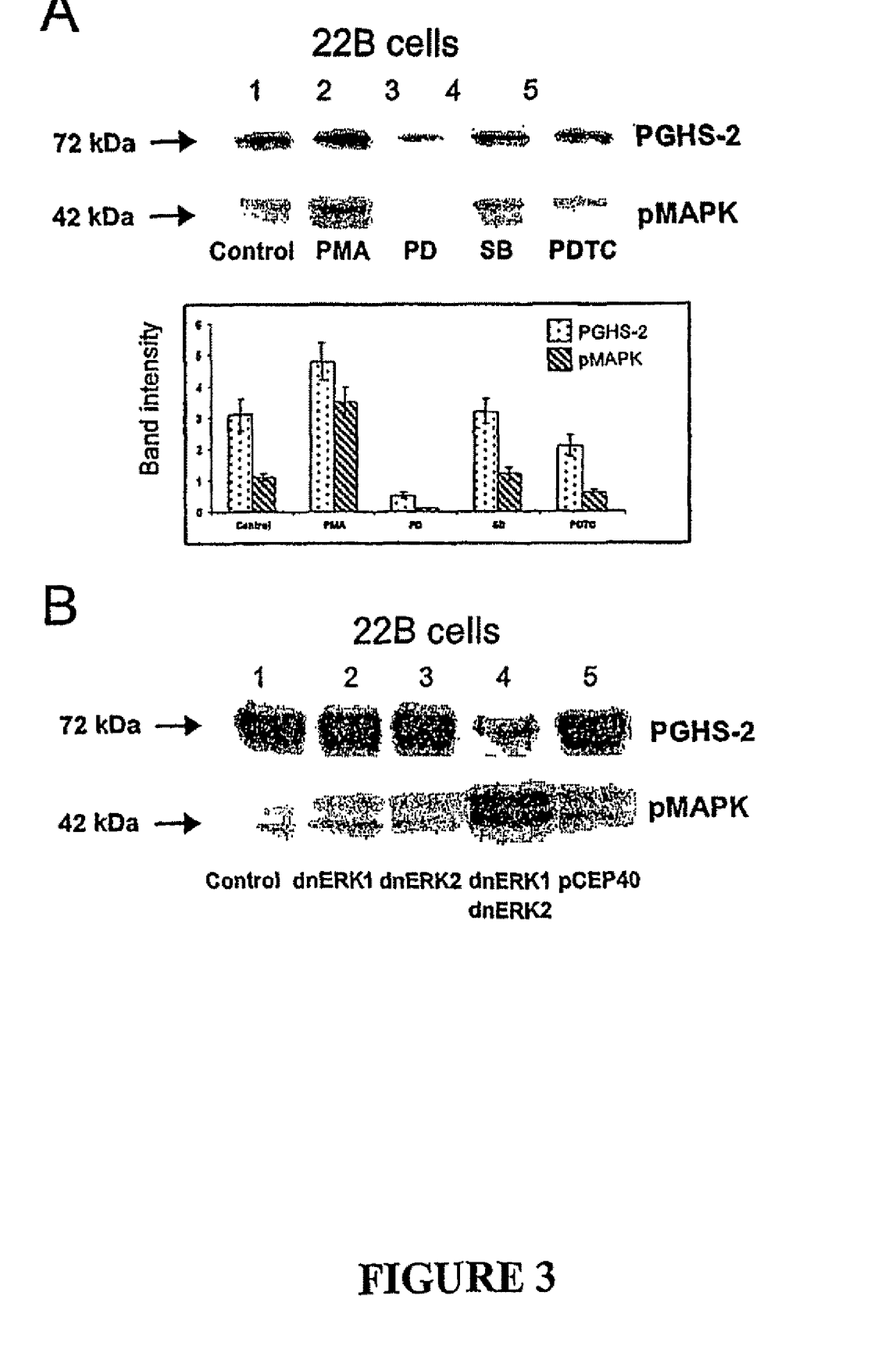
FIG. 3. Expression of PGHS-2 in UM-SCC-22B (22B) cells is attenuated by inhibitors of either MAPK, p38 or NF-κB.

Evidence developed elsewhere indicates that MAPK, p38 and NF-κB play important roles in up-regulation of PGHS-2 in response to cytokines and growth factors in normal cells (Goppelt-Struebe et al., 2000; Wang and Tai, 1998). We therefore studied whether MAPK, p38 and NF-κB were implicated in the constitutive expression of PGHS-2 in cancer cells. When confluent UM-SCC-22B cells were treated for 12 h with PD98059 (10 μM), an inhibitor of the MAPK cascade at MAPK kinase (MEK), PGHS-2 protein decreased to very low levels. SB23058, a p38 kinase pathway inhibitor, and pyrrolidine dithiocarbamate (PDTC), an inhibitor of NF-$_K$B, minimally inhibited PGHS-2 expression in UM-SCC-22B cells (FIG. 3A). Although PKC is integral to constitutive expression of PGHS-2 in the tumor cell lines studied here, and PMA is shown to increase PGHS-2 levels in this figure, these results indicate that there are multiple intracellular signaling pathways involved in constitutive expression of PGHS-2 in UM SCC-22B cells.

We transfected UM-SCC-22B cells with dominant negative ERK1 and/or ERK2 expression plasmids. Individually, dnERK1 or dnERK2 had little effect on PGHS-2 expression (FIG. 3B). As expected, dnER1 and 2 together inhibited kinase activity of both isoforms leading to decreased PGHS-2 expression, although phosphorylation of the mutant ERKs was seen (FIG. 3B). This latter response has previously been described by Robbins et al. (1992). This set of results suggests that constitutive expression of PGHS-2 in prostate cancer cells is in part dependent on the MAPK and NF-KB signal transduction pathways.

PGE2 Elaboration by Cancer Cells and ECV 304 Cells

Figure 4:
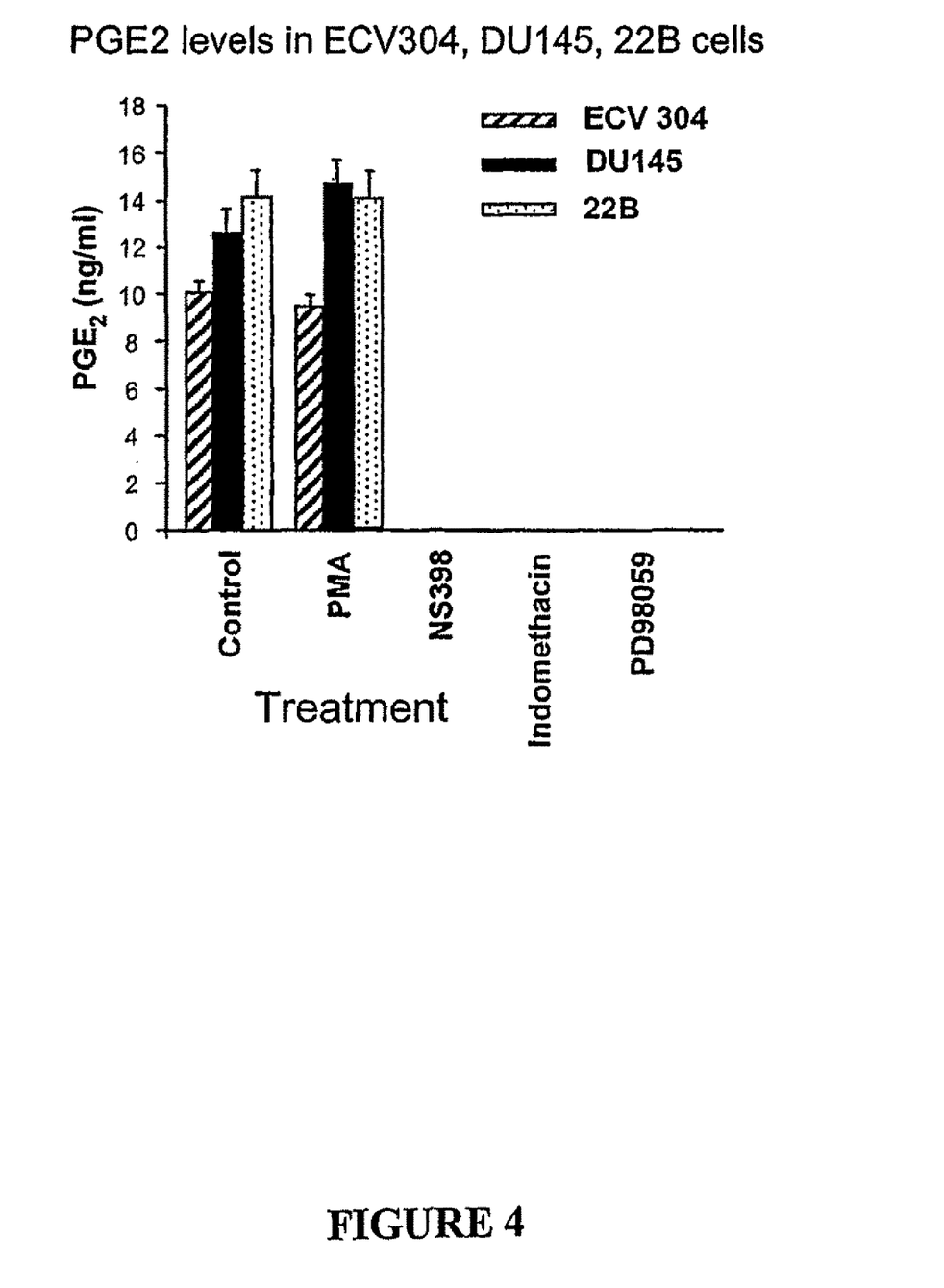
FIG. 4. $PGE_2$ production in ECV 304, UM-SCC-22B (22B) and DU145 cells.

Prostate and head and neck cancer cells produced levels of $PGE_2$ (12.7±1.3 ng/ml, and 14.3±1.5 ng/ml [mean±SD], respectively) that were similar to those of noncancerous endothelial cells (ECV 304, 10.1±1.2 ng/ml) (FIG. 4). PMA (100 nM) has been shown elsewhere to enhance $PGE_2$ production in a number of cell lines (Habib et al., 1995; Molina-Holgado et al., 2000). In the present studies, however, PMA did not significantly increase $PGE_2$ production in either DU145 or UM-SCC-22B cells (FIG. 4). PD98059 decreased $PGE_2$ production in cancer cells to basal levels, as did indomethacin, a non-specific inhibitor of PGHS-1 and PGHS-2, and NS398, a selective inhibitor of PGHS-2. Although PMA-induced increased expression of PGHS-2 did not result in significantly higher levels of $PGE_2$ production in DU145 and UM-SCC-22B cells, $PGE_2$ production was subject to down-regulation by conventional inhibitors of PGHS-2 enzyme activity.

Figure 5:
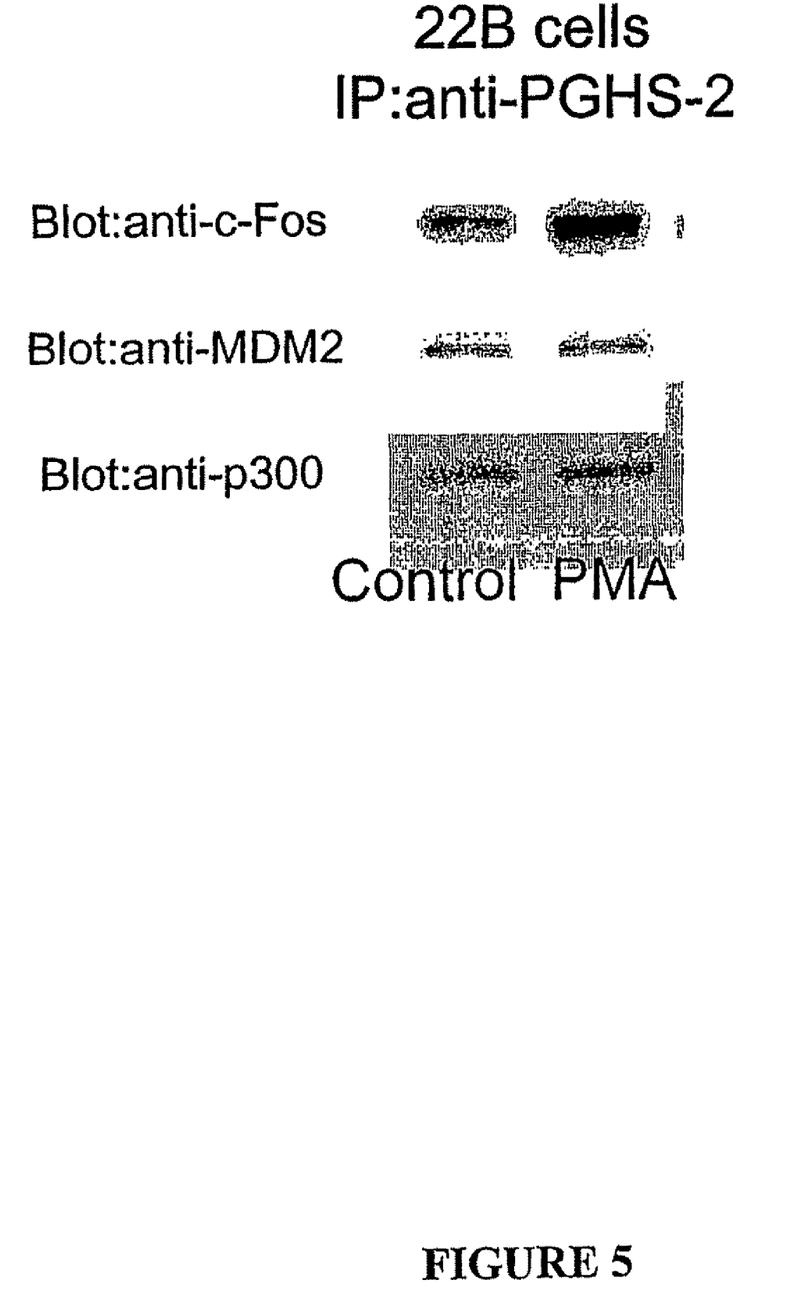
FIG. 5. PGHS-2 is associated with c-Fos, MDM2 and p300

Association of Nuclear PGHS-2 with Other Transcriptional Activators in Cancer Cell Lines To investigate whether PGHS-2 associates with transcriptionally-active nucleoproteins, double antibody staining experiments were carried out in quiescent UM-SCC-22B cells, and demonstrated that c-Fos and PGHS-2 co-localized in cell nuclei (FIG. 5). Co-immunoprecipitation studies also indicated that nuclear PGHS-2 associates with MDM2 and with the nuclear coactivator protein p300. MDM2 is a determinant of the turnover of p53 and, when bound to p53, facilitates nuclear export of the oncogene suppressor protein (Momand et al., 1992). The treatment of UM-SCC-22B cells with PMA, 100 nM, caused a marked increase in nuclear association of PGHS-2 with c-Fos (FIG. 5), but little increase in association with MDM2 or p300.

Figure 6:
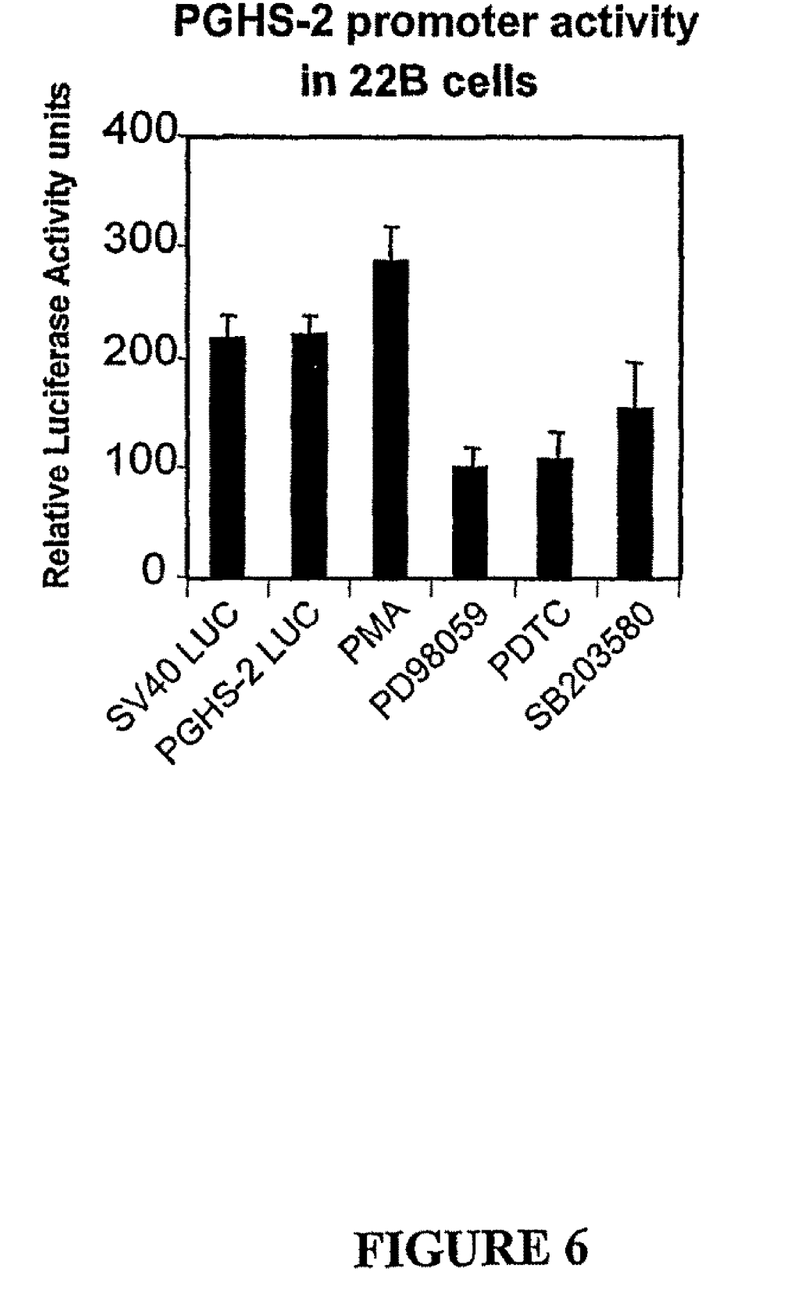
FIG. 6. Quiescent UM-SCC-22B (22B) cells in culture exhibit substantial PGHS-2 promoter activity UM-SCC-22B cells were transfected with the −831/+123 PGHS-2 promoter constructs fused to a luciferase reporter or the luciferase reporter with the SV 40 promoter (pGL2 promoter).

PGHS-2 Binding to PGHS-2 Promoter and to Other Genes that Modulate Cell Division To assess PGHS-2 promoter activity in UM-SCC-22B cells, the proximal −831/+123 base pairs of the human PGHS-2 promoter were fused to a luciferase reporter (pGHS-2 LUC) (Cao et al., 1999). This PGHS-2 reporter or SV40 LUC (pGL2 promoter) were transfected into near confluent UM-SCC-22B tumor cells. As FIG. 6 indicates, PGHS-2 promoter activity was readily detected in quiescent UM-SCC-22B cells and was similar to that obtained with transfection of the SV 40 promoter and luciferase reporter. This result is consistent with the constitutive expression of PGHS-2 found in UM-SCC-22B cells. While PMA (100 nM) only negligibly increased PGHS-2 promoter activity, treatment of cells with PD98059, PDTC, or SB203580 inhibited PGHS-2 promoter activity. These results implicate the MAPK signal transduction pathway and NF-κB in constitutive expression of PGHS-2.

Figure 7:
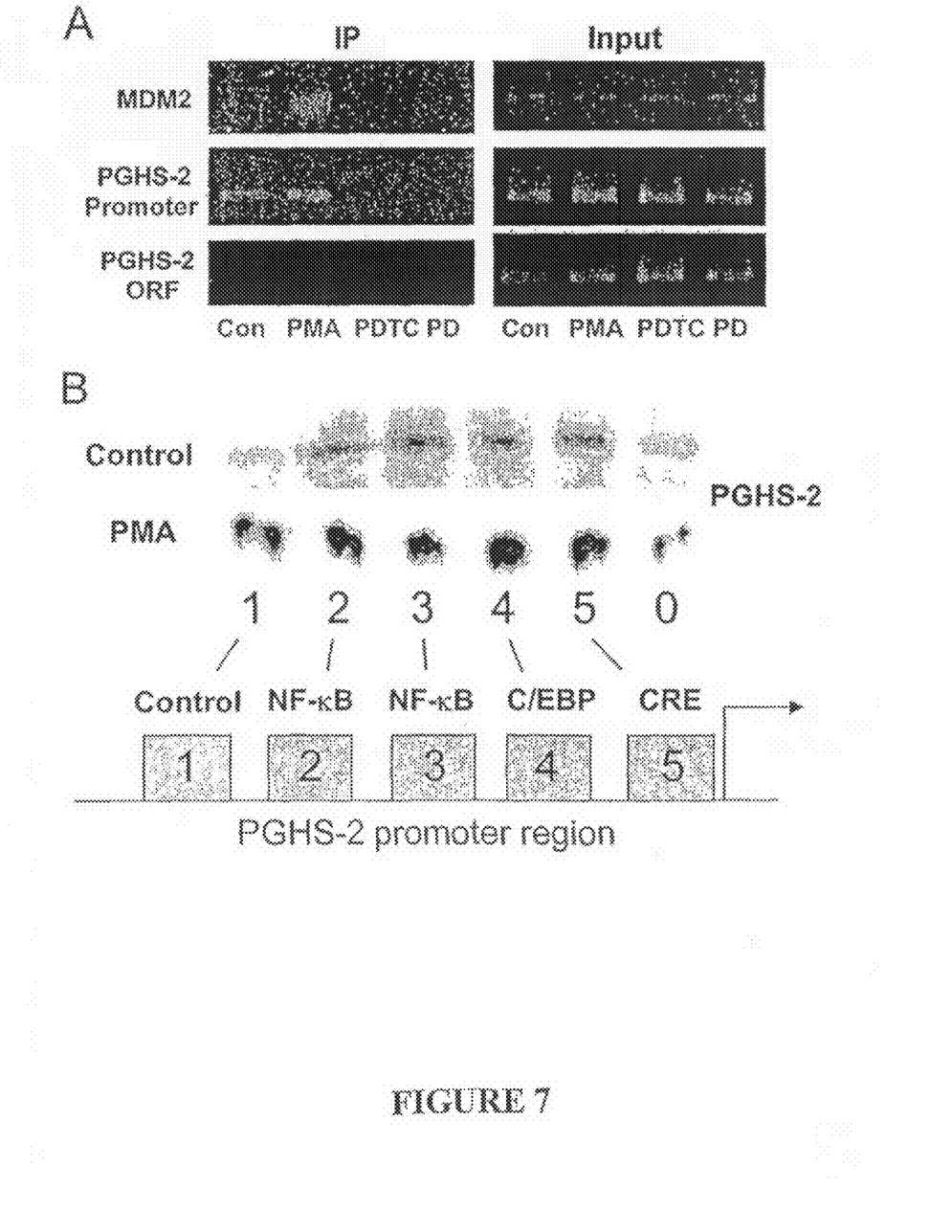
FIG. 7. Chromatin immunoprecipitation (ChIP) analysis of PGHS-2 binding to the PGHS-2 promoter A: ChIP was performed with PGHS-2 antibody, using UM-SCC-22B (22B) cells constitutively expressing PGHS-2, and in the absence (Con) or presence of PMA (100 nM), PDTC (100 μM) or PD98059 (PD, 10 μM) for 12 h. Input and immunoprecipitated (IP) DNA was amplified by using primers for MDM2, PGHS-2 promoter and PGHS-2 ORF, and the amplified DNAs were then separated by electrophoresis and scanned with the VersaDOC™ Imaging System.

In ChIP experiments in prostate cancer cells, using monoclonal anti-PGHS-2, we compared the amount of immunoprecipitable PGHS-2 promoter sequence with the amount of input DNA for each sample; a PGHS-2 ORF primer served as a negative control. We found that PGHS-2 bound constitutively to the PGHS-2 promoter, and PMA treatment of cells resulted in minimal increases in binding of PGHS-2 to the promoter (FIG. 7 A). PGHS-2 also bound to the promoter region of MDM2. Binding of PGHS-2 to both promoters was inhibited by PDTC and PD98059, suggesting dependence of these effects on NF-κB and MAPK activation.

We next defined which domains of the PGHS-2 promoter were capable of binding PGHS-2 protein. We used a DNA-protein binding assay in which a biotinylated short PGHS-2 promoter oligonucleotide probe was incubated with streptavidin-coated beads previously interacted with nuclear extract proteins. As shown in FIG. 7B, PGHS-2 bound to c/EBP, CRE, and two NF-$_K$B sites on the PGHS-2 promoter. There was only weak binding to the DNA sequence between the two NF-$_K$B sites in the PGHS-2 promoter region.

Figure 8:
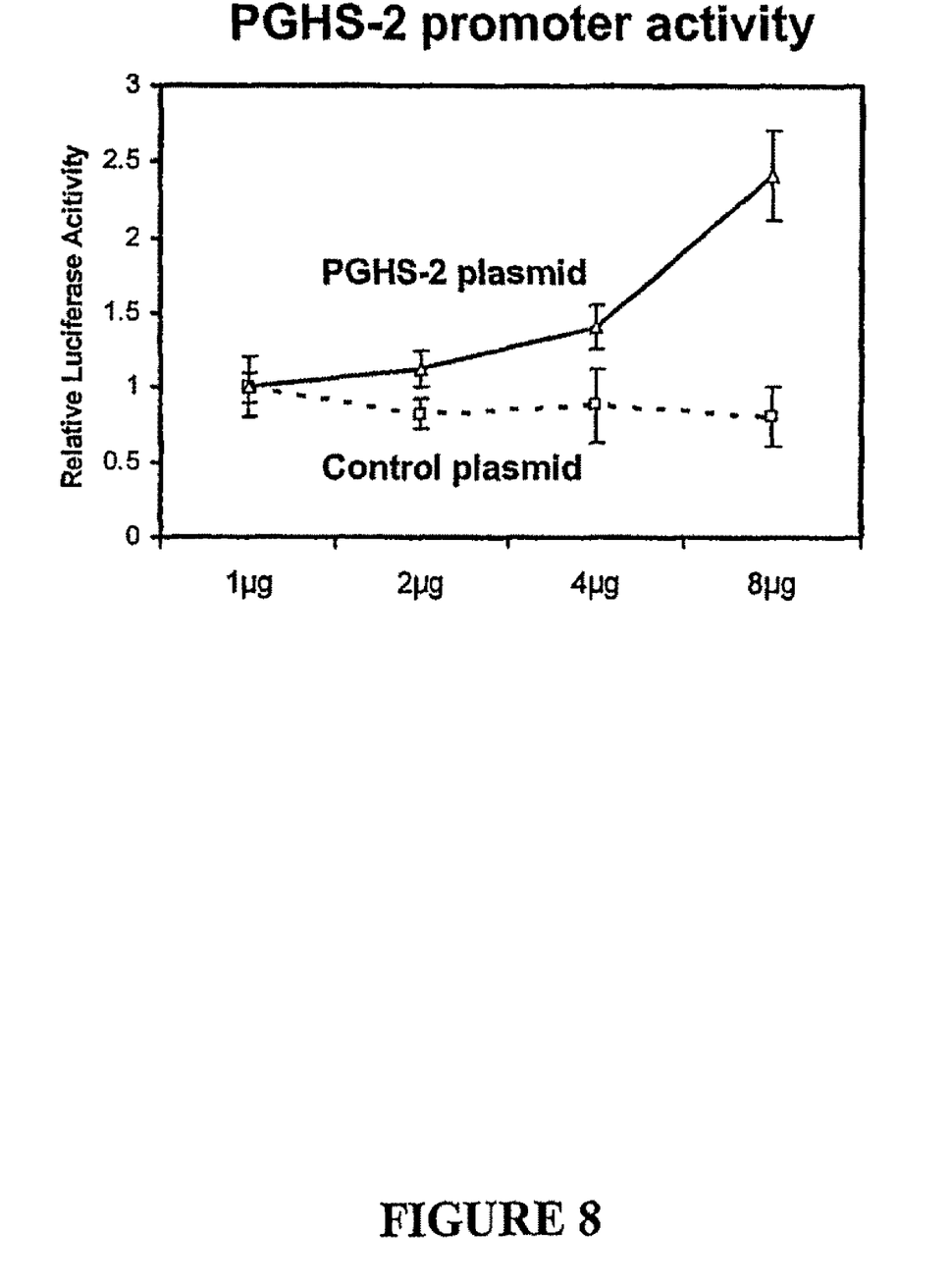
FIG. 8. PGHS-2 protein increases PGHS-2 promoter activity in 293T cells

We also determined whether binding of PGHS-2 to its own promoter had any effect on transcriptional activity of the promoter. A PGHS-2 promoter-driven luciferase plasmid was co-transfected with PGHS-2 expression plasmids into 293T cells. These cells were used because of their low endogenous content of PGHS-2, as alterations in transcriptional activity of PGHS-2 could not be assessed in cell lines in which the gene is constitutively expressed. When the amount of PGHS-2 protein was increased in 293T cells at 24 h after transfection of PGHS-2 expression plasmids, luciferase activity was increased (FIG. 8). Thus, the binding of PGHS-2 to its own promoter provided positive feedback on PGHS-2 gene transcription. In contrast, transfection of the empty expression vector did not affect PGHS-2 promoter activity.

Discussion

Much recent attention has been directed at PGHS enzymes in cancer cells (Zimmermann et al., 1999; Yoshimura et al., 2000; Yu et al., 2002; Xiong et al., 2003). Located in the cytoplasm, particularly in the perinuclear region and in endoplasmic reticulum, these enzymes are involved in prostanoid production that by several mechanisms can support tumor growth (Gately, 2000; Hendrickx et al., 2003; Pai et al., 2002). Constitutively-expressed PGHS-1 has been assumed to be particularly relevant in this regard, because PGHS-2 is seen as an inducible enzyme with important roles in inflammatory responses in which noncancerous cells participate (Cao et al., 2003; Cao and Smith, 1999; Han et al., 2002). Evidence from several laboratories, however, indicates that PGHS-2 may be constitutively expressed in cancer cells (Howe et al., 2001; Hanahan and Weinberg, 2000). Indeed, PGHS-2 was found in the current studies to be constitutively expressed in human prostate and head and neck cancer cell lines, but not in an immortalized noncancerous endothelial cell line (ECV 304). The possible significance of such findings is suggested by observations that nonsteroidal anti-inflammatory drugs (NSAIDs) that inhibit the enzymatic activity of both PGHS-1 and PGHS-2 can serve a protective function against development of several tumors (Arber and DuBois, 1999; Moran E M, 2002; Oshima et al., 1996; Davies G L, 2003; Piazuelo et al., 2003; Parfenova et al., 2001).

Confocal microsocopy in the present studies revealed that PGHS-2 protein was not only found in a perinuclear location, but was abundant within the nucleus of these cancer cell lines. Although PGHS-2 protein has been reported to be present in the nucleus of noncancerous cells, this translocation of PGHS-2 has been the result of cytokine treatment or other manipulations and has not been constitutive (Parfenova et al., 2001; Marvin et al., 2000). Our finding of nuclear PGHS-2 was confirmed by two techniques (confocal microscopy, cell fractionation) and caused us to investigate the possibility that PGHS-2 has a transcriptional function distinct from its well-described enzymatic role.

Chromatin immunoprecipitation studies revealed that PGHS-2 bound to the promoter region of PGHS-2 in human prostate and head and neck cancer cell lines. We identified the several specific domains of the PGHS-2 promoter region in which DNA-PGHS-2 protein interactions occurred. In transcriptional studies carried out in 293T cells into which the relevant constructs were transfected, we showed that PGHS-2 protein was capable of directly regulating the transcription of its own gene. Extrapolating these results to cancer cells, we propose that a mechanism of the 'constitutive' expression of the PGHS-2 gene in cancer cells may be the transactivator function of its own gene product.

Several lines of evidence have implicated NF-KB, mitogen-activated protein kinase, C/EBP and CRE involvement in upregulation of PGHS-2 proteins (Zhu et al., 2002). Using a protein-DNA binding assay, we found that PGHS-2 in fact bound strongly to two NF-KB sites and to C/EBP and CRE sites of the PGHS-2 promoter region. PGHS-2 bound only weakly to control sequences between two NF-KB sites of the PGHS-2 promoter. We did not determine whether PGHS-2 directly binds to its own promoter or binds in association with other activators.

An additional finding was that PGHS-2 protein bound to the MDM2 promoter. If PGHS-2 functions as a transactivator for MDM2, then this becomes a mechanism by which the cancer cell that constitutively expresses PGHS-2 may regulate cellular levels of the oncogene suppressor protein, p53. MDM2 binds to the transcriptional activation domain of p53 in the nucleus and causes translocation of the protein to the cytoplasm where p53 is rapidly degraded (Momand et al., 1992).

The present studies also revealed that PGHS-2 complexed with several nucleoproteins. These proteins include c-Fos, which, when bound to c-Jun, is a transactivator (AP-1) (Jang et al., 1996). AP-1 is involved in the induction of the PGHS-2 gene (Subbaramaiah et al., 2002; Guo et al., 2001), but a direct interaction of AP-1 and PGHS-2 has not previously been described. This interaction raises the possibility, as yet unstudied, that PGHS-2 may be transcriptionally active as a heterodimer with c-Fos. The co-activator protein p300 was also found to complex with PGHS-2. This was not surprising since p300 has intrinsic transacetylase activity that has been shown to be relevant to transcription of the PGHS-2 gene (Deng et al., 2003). Finally, nuclear PGHS-2 bound to MDM2 protein, as well as to the MDM2 promoter. While the significance of this finding is not yet clear, the possibility exists that, like p53, PGHS-2 is subject to nuclear export and turnover that is directed by MDM2.

EXAMPLES

Cell Lines

The human head and neck cancer cell line UM-SCC-22B was maintained in DMEM supplemented with 10% fetal bovine serum (FBS). DU145 human prostate cancer cells were cultured in Eagle's minimal essential medium supplemented with 10% FBS. ECV 304 endothelial cells were grown in M199 medium that contained 10% FBS. 293T cells were grown to 60% confluence in DMEM with 5% FBS. All cell cultures were maintained in a 5% C02/95% 02 incubator at 37° C. Signal transduction reagents used in cell treatments included PD98059 and SB203580, obtained from Calbiochem, La Jolla, Calif., and PDTC and PMA, obtained from Sigma-Aldrich, St. Louis, Mo.

Cell Fractionation

Fractionation of cells in a microfuge and preparation of nucleoproteins was by a previously reported method (Lin et al., 2002). Nuclear extracts were prepared by resuspension of the crude nuclear fraction in high salt buffer (420 mN NaCl, 20% glycerol) at 4° C. with rocking for 1 h. The supernatants were then collected after subsequent centrifugation at 4° C. and 13,000 rpm for 10 min.

Immunoprecipitation and Immunoblotting

The techniques used were those previously described by our laboratory (Lin et al., 1999). In brief, nucleoproteins were separated on discontinuous SDS-PAGE (9% gels) and then transferred by electroblotting to Immobilon membranes (Millipore, Bedford, Mass.). After blocking with 5% milk in Tris-buffered saline containing 0.1% Tween, the membranes were incubated with various antibodies overnight. Secondary antibodies were either goat anti-rabbit IgG (1:1000) or rabbit anti-mouse IgG (1:1000) (Dako, Carpenteria, Calif.), depending upon the origin of the primary antibody. Immunoreactive proteins were detected by chemiluminescence.

Plasmid Transfection and Luciferase Assay

293T Cells were transfected with dominant negative plasmids, or with vector alone, using Lipofectamine Plus (Invitrogen) according to the supplier's instructions. Aliquots of cells from each treatment group were then exposed to the experimental variables and subsequently harvested for preparation of nuclear proteins. An internal control plasmid, p-galactosidase, was co-transfected in all experiments for normalization of results.

Confocal Microscopy

ECV 304, UM-SCC-22B and DU145 cells were cultured in slide chambers, were washed in phosphate-buffered saline (PBS), fixed by incubation for 10 min in 2% formaldehyde in PBS and then washed twice with PBS. Monoclonal antibodies to PGHS-1, PGHS-2 (Cayman, Ann Arbor, Mich.) or c-Fos (Santa Cruz, Santa Cruz, Calif.) were diluted 1:200 in PBS, then added to the chamber and the samples incubated for 45 min. Following washing in PBS, the samples were incubated for 30 min with a 1:100 dilution of FITC-conjugated rabbit anti-mouse IgG in PBS. A Zeiss scanning confocal microscope (510LS) with an argon ion laser as the excitation source was used for microscopy. 25× and 60× objectives and a 50% laser power source were used for subcellular localization of PGHS-1 and PGHS-2.

Transfection of Dominant Negative Plasmids of MAPK (ERK1/2) and p38 Kinase

Plasmids containing fragments of the human PGHS-2 promoter were generously provided by Dr. S. M. Prescott, University of Utah, Salt Lake City, Utah (Meade et al., 1999). The plasmid −1800pGL2 contained −1840/+123, and plasmid +800pGL2 contained the sequence −831/+123. pSV-f3-galactosidase was used as a transfection efficiency control. Dominant negative plasmids of MAPK (ERK1/2) were a gift of Dr. Melanie Cobb (University of Texas Southwestern, Dallas, Tex.). Using Lipofectamine Plus, 60% confluent UM-SCC-22B cells in 10 cm plates were transfected with approximately 6 ug of plasmids of dominant negative ERKI and ERK2. Cultures were incubated at 37° C. for 5 h. The medium was replaced with 10% fetal bovine serum containing medium for 24 h and then with serum-free medium for 24 h. Transfected cells were incubated with 100 nM phorbol-12-myristate-13-acetate (PMA, Sigma, St. Louis, Mo.) for 12 h and subsequently harvested for western blot analysis of PGHS-2 protein levels.

Chromatin Immunoprecipitation (ChIP)

Chromatin immunoprecipitation was performed as described by Luo et al. (1998) and Braunstein et al. (1996). Aliquots of cells ($6 \times 10^6$) in monolayers were treated with 1% formaldehyde for 15 min at room temperature to effect crosslinking. Monolayers were then washed twice with PBS. Extracts were prepared by scraping cells in 1 ml of buffer (150 mM NaCl, 1% NP-40, 0.5% DOC, 0.1% SDS, 50 mM Tris [pH 8.0], 5 mM EDTA) that contained the protease inhibitors leupeptin (10 .mu.g/ml) and pepstatin A (10 .mu.g/ml), phosphatase inhibitors (50 mM NaF and 0.2 mM sodium orthovanadate) and the deacetylase inhibitor, trichostatin A, 5 .mu.M (Calbiochem, San Diego, Calif.). Cell lysates were sonicated to yield chromatin fragments of approximately 600 bp, as assessed by agarose gel electrophoresis. Immunoprecipitation was carried out with anti-p53 (Santa Cruz, Santa Cruz, Calif.), anti-phosphoSer392-p53 (Cell Signaling, Beverly, Mass.), or anti-acetylated p53 (Upstate Biotechnology, Lake Placid, N.Y.). For studies of the PGHS-2 promoter, anti-PGHS-2 (Cayman) was used. Primers used in PCR were for promoters of MDM2 [5'-GGA TTGGGCCGGT-TCAGTGG-3' (SEQ ID NO:1) (forward) and 5'-GGTCT ACCCTCCAA-TCGCCAC-3' (SEQ ID NO:2) (reverse)]; PGHS-2 [5'-CTGTTGAAAGCAACTTAGCT-3' (SEQ ID NO:3) (forward) and 3'-AGACTGAAA ACCAAGCCCAT-3' (SEQ ID NO:4) (reverse)]. PCR results were resolved by 1% agarose gel electrophoresis, and gels were stained with ethidium bromide. Relative levels of DNA were determined with QuantifyOne software (Bio-Rad Laboratories, Inc., Hercules, Calif.).

DNA-Binding Assay

Aliquots (200 μg) of nuclear extract proteins containing 6 μg biotinylated PGHS-2-specific NF-κB, C/EBP, or CRE sequences (Invitrogen) and 60 μl of 4% streptavidin-coated beads were incubated for 1 hour with shaking. The streptavidin-coated beads, with associated nuclear extract proteins bound to the biotinylated probe, were pelleted and washed three times with cold PBS. Proteins bound to the beads were eluted by boiling and were separated on SDS-PAGE. Western blot analysis was carried out with anti-human PGHS-2 antibody as described above.

REFERENCES

Arber, N., and DuBois, R N. (1999). Nonsteroidal anti-inflammatory drugs and prevention of colorectal cancer. CUff Gastroenterol Rep 1,441-448.

Braunstein, M., Sobel, R. E., Allis, C. D., Turner, R M., and Broach, I R (1996). Efficient transcriptional silencing in *Saccharomyces cerevisiae* requires a heterochromatin histone acetylation pattern. Mol Cell Biol 16, 4349-4356.

Cao, H. J., Wang, H. S., Zhang, Y., Lin, H. Y., Phipps, R. P., and Smith, T. J. (1998). Activation of human orbital fibroblasts through CD40 engagement results in a dramatic induction of hyaluronan synthesis and prostaglandin endoperoxide H synthase-2 expression. Insights into potential pathogenic mechanisms of thyroid-associated ophthalmopathy. J Biol Chem 273, 29615-29625.

Cao, H. J., and Smith, T. J. (1999). Leukoregulin upregulation of prostaglandin endoperoxide H synthase-2 expression in human orbital fibroblasts. Am J Physiol 277, C1075-1085.

Cao, H. J., Han, R, and Smith, T. J. (2003). Robust induction of PGHS-2 by IL-1 in orbital fibroblasts results from low levels of IL-1 receptor antagonist expression. Am J Physiol Cell Physiol 284, CI429-1437.

Carey, T. E., Kimmel, K. A., Schwartz, D. R, Richter, D. E., Baker, S. R, and Krause, C. J. (1983). Antibodies to human squamous cell carcinoma. Otolarygnol Head and Neck Surg 91, 482-491.

Davies, G. L. (2003). Cyclooxygenase-2 and chemoprevention of breast cancer. J Steroid Biochem Mol Biol 86, 495-499.

Davies, G., Martin, L. A., Sacks, N., and Dowsett, M. (2002). Cyclooxygenase-2 (COX-2), aromatase and breast cancer: a possible role for COX-2 inhibitors in breast cancer chemoprevention. Ann Oncol 13, 669-678.

Deng, W. G., Zhu, Y, and Wu, K. K. (2004). Role of p300 and PCAF in regulating cyclooxygenase-2 promoter activation by inflammatory mediators. Blood 103, 2135-2142.

Funk, C. D., Funk, L. B., Kennedy, M. E., Pong, A S., and Fitzgerald, G. A. (1991). Human platelet/erythroleukemia cell prostaglandin GIH synthase: cDNA cloning, expression, and gene chromosomal assignment. FASEB J 5, 2304-2312.

Gately, S., and Li, W. W. (2004). Multiple roles of COX-2 in tumor angiogenesis: a target for antiangiogenic therapy. Semin Oncol 31, 2-11.

Goppelt-Struebe, M., Rehm, M., and Schaefers, H. J. (2000). Induction of cyclooxygenase-2 by platelet-derived growth factor (PDGF) and its inhibition by dexamethasone are independent of NF-kappaB/IkappaB transcription factors. Naunyn Schmiedebergs Arch Pharmacol 361, 636-645.

Guo, Y. S., Hellmich, M. R., Wen, X. D., and Townsend, C. M., Jr. (2001). Activator protein-1 transcription factor mediates bombesin-stimulated cyclooxygenase-2 expression in intestinal epithelial cells. J Biol Chem 276, 22941-22947.

Habib, A, Martinuzzo, M. B., Carreras, L. a., Levy-Toledano, S., and Maclouf, J. (1995). Increased expression of inducible cyclooxygenase-2 in human endothelial cells by antiphospholipid antibodies. Thromb Haemost 74, 770-777.

Han, R., Tsui, S., and Smith, T. J. (2002). Up-regulation of prostaglandin E2 synthesis by interleukin-1 beta in human orbital fibroblasts involves coordinate induction of prostaglandinendoperoxide H synthase-2 and glutathione-dependent prostaglandin E2 synthase expression. J Biol Chem 277, 16355-16364.

Hanahan, D., and Weinberg, R. A (2000). The hallmarks of cancer. Cell 100, 57-70.

Hendrickx, N., Volanti, C., Moens, u., Seternes, a. M, de Witte, P., Vandenheede, J. R., Piette, J., and Agostinis, P. (2003). Up-regulation of cyc100xygenase-2 and apoptosis resistance by p38 MAPK in hypericin-mediated photodynamic therapy of human cancer cells. J Biol Chem 278, 52231-52239.

Hoshino, T., Tsutsumi, S., Tomisato, W., Hwang, H. J., Tsuchiya, T., and Mizushima, T. (2003). Prostaglandin E2 protects gastric mucosal cells from apoptosis via EP2 and EP4 receptor activation. J Biol Chem 278, 12752-12758.

Howe, L. R., Subbaramaiah, K., Brown, A M., and Dannenberg, A. J. (2001). Cyc100xygenase-2: a target for the prevention and treatment of breast cancer. Endocr Relat Cancer 8, 97-114.

Ishaque, A., Dunn, M. J., and Sorokin, A (2003). Cyclooxygenase-2 inhibits tumor necrosis factor alpha-mediated apoptosis in renal glomerular mesangial cells. J Biol Chem 278, 10629-10640.

Jang, S. L, Steinert, P. M., and Markova, N. G. (1996). Activator protein 1 activity is involved in the regulation of the cell type-specific expression from the proximal promoter of the human profilaggrin gene. J Biol Chem 271, 24105-24114.4.

Kujubu, D. A, Reddy, S. T., Fletcher, B. S., and Herschman, H. R. (1993). Expression of the protein product of the prostaglandin synthase-2/TIS10 gene in mitogen-stimulated Swiss 3T3 cells. J Biol Chem 268, 5425-5430.

Lim, J. W., Kim, H., and Kim, K. H. (2002). Expression of Ku70 and Ku80 mediated by NF-kappa B and cyclooxygenase-2 is related to proliferation of human gastric cancer cells. J Biol Chem 277, 46093-46100.

Lin, R. Y., Davis, F. B., Gordinier, J. K., Martino, L. J., and Davis, P. J. (1999). Thyroid hormone induces activation of mitogen-activated protein kinase in cultured cells. Am J Physiol 276, C1014-1024.

Lin, H. Y., Shih, A., Davis, F. B., Tang, R. Y., Martino, L. J., Bennett, J. A., and Davis, P. J. (2002). Resveratrol induced serine phosphorylation of p53 causes apoptosis in a mutant p53 prostate cancer cell line. J Urol 168, 748-755.

Liou, J. Y., Deng, W. G., Gilroy, D. W., Shyue, S. K., and Wu, K. K. (2001). Colocalization and interaction of cyclooxygenase-2 with caveolin-1 in human fibroblasts. J Biol Chem 276, 34975-34982.

Luo, R. x., Postigo, A. A., and Dean, D. C. (1998). Rb interacts with histone deacetylase to repress transcription. Cell 92, 463-473.

Marvin, K. W., Eykholt, R. L., and Mitchell, M. D. (2000). Subcellular localization of prostaglandin R synthase-2 in a human amnion cell line: implications for nuclear localized prostaglandin signaling pathways. Prostaglandins Leukot Essent Fatty Acids 62, 7-11.

Meade E. A., McIntyre, T. M., Zimmerman, G. A., and Prescott, S. M. (1999). Perioxisome proliferators enhance cyclooxygenase-2 expression in epithelial cells. J Biol Chem 274, 8328-8334.

Molina-Rolgado, E., Ortiz, S., Molina-Rolgado, F., and Guaza, C. (2000). Induction of COX-2 and PGE(2) biosynthesis by IL-1 beta is mediated by PKC and mitogen-activated protein kinases in murine astrocytes. Br J Pharmacol 131, 152-159.

Momand, J., Zambetti, G. P., Olson, D. C., George, D., and Levine, A J. (1992). The mdm-2 oncogene product forms a complex with the p53 protein and inhibits p53-mediated transactivation. Cell 69, 1237-1245.

Moran, E. M. (2002). Epidemiological and clinical aspects of nonsteroidal anti-inflammatory drugs and cancer risks. J Environ Pathol Toxicol Oncol 21, 193-201.

Morita, I., Smith, W. L., DeWitt, D. L., and Schindler, M. (1995). Expression-activity profiles of cells transfected with prostaglandin endoperoxide H synthase measured by quantitative fluorescence microscopy. Biochemistry 34, 7194-7199.

Oshima, M., Dinchuk, J. E., Kargman, S. L., Oshima, H., Hancock, B., Kwong, E., Trzaskos, J. M., Evans, J. F., and Taketo, M. M. (1996). Suppression of intestinal polyposis in Apc delta716 knockout mice by inhibition of cyclooxygenase 2 (COX-2). Cell 87, 803-809.

Pai, R., Soreghan, B., Szabo, I. L., Pavelka, M., Baatar, D., and Tamawski, A S. (2002). Prostaglandin E2 trans activates EGF receptor: a novel mechanism for promoting colon cancer growth and gastrointestinal hypertrophy. Nat Med 8, 289-293.

Pang, L., Nie, M., Corbett, L., Donnelly, R., Gray, S., and Knox, A J. (2002). Protein kinase C-epsilon mediates bradykinin-induced cyclooxygenase-2 expression in human airway smooth muscle cells. Faseb J 16, 1435-1437.

Parfenova, H., Parfenov, V. N., Shlopov, B. V., Levine, V., Falkos, S., Pourcyrous, M., and Leffler, C. W. (2001). Dynamics of nuclear localization sites for COX-2 in vascular endothelial cells. Am J Physiol Cell Physiol 281, C166-178.

Patel, V. A., Dunn, M. J., and Sorokin, A (2002). Regulation of MDR-1 (P-glycoprotein) by cyclooxygenase-2. J Biol Chem 277, 38915-38920.

Piazuelo, E., Jimenez, P., and Lanas, A (2003). COX-2 inhibition in esophagitis, Barrett's esophagus and esophageal cancer. Curr Pharm Des 9, 2267-228024.

Robbins, D. J., Zhen, E., Owaki H., Vanderbilt, C. A., Ebert, D., Geppert, T. D., and Cobb, M. H. (1993). Regulation and properties of extracellular signal-regulated protein kinases 1 and 2 in vitro. J Biol Chem 268, 5097-5106.

Rollins, T. E., and Smith, W. L. (1980). Subcellular localization of prostaglandin-forming cyclooxygenase in Swiss mouse 3T3 fibroblasts by electron microscopic immunocytochemistry. J Biol Chem 255, 4872-4875.

Smith, W. L., Rollins, T. E., and DeWitt, D. L. (1981). Subcellular localization of prostaglandin forming enzymes using conventional and monoclonal antibodies. Prog Lipid Res 20, 103-110.

Smith, W. L., Garavito, R. M., and DeWitt, D. L. (1996). Prostaglandin endoperoxide H synthases (cyclooxygenases)-1 and -2. J Biol Chem 271, 33157-33160.2.

Smith, W. L., and Dewitt, D. L. (1996). Prostaglandin endoperoxide H synthases-1 and -2. Adv Immuno 162, 167-215.

Smith, W. L., DeWitt, D. L., and Garavito, R. M. (2000). Cyclooxygenases: structural, cellular, and molecular biology. Annu Rev Biochem 69, 145-182.

Subbaramaiah, K., Norton, L., Gerald, W., and Dannenberg, A. J. (2002). Cyclooxygenase-2 is overexpressed in HER-2/neu-positive breast cancer: evidence for involvement of AP-1 and PEA3. J Biol Chem 277, 18649-18657.

Wang, D., and Dubois, R. N. (2004). Cyclooxygenase-2: a potential target in breast cancer. Semin Oncol 31 (1 Suppl3), 64-73.

Wang, Z., and Tai, H. H. (1998). Interleukin-1 beta and dexamethasone regulate gene expression of prostaglandin H synthase-2 via the NF-κB pathway in human amnion derived WISH cells. Prostaglandins Leukot Essent Fatty Acids 59, 63-69.

Wulfing, C., Eltze, E., von Struensee, D., Wulfing, P., Hertle, L., and Piechota, H. (2004). Cyclooxygenase-2 expression in bladder cancer: correlation with poor outcome after chemotherapy. Eur Urol 45, 46-52.

Xiong, B., Sun, T. J., Yuan, H. Y., Hu, M. B., Hu, W. D., and Cheng, F. L. (2003). Cyclooxygenase-2 expression and angiogenesis in colorectal cancer. World J Gastroenterol 9, 1237-1240.

Xu, X. M., Ohashi, K., Sanduja, S. K., Ruan, K. R., Wang, L. H., and Wu, K. K. (1993). Enhanced prostacyclin synthesis in endothelial cells by retrovirus-mediated transfer of prostaglandin H synthase cDNA J Clin Invest 91, 1843-1849.

Yoshimura, R., Sano, H., Masuda, c., Kawamura, M., Tsubouchi, Y., Chargui, J., Yoshimura, N., Hla, T., and Wada, S. (2000). Expression of cyclooxygenase-2 in prostate carcinoma. Cancer 89, 589-596.

Yu, H. P., Xu, S. Q., Liu, L., Shi, L. Y., Cai, X. K., Lu, W. H., Lu, B., Su, Y. H., and Li, Y. Y. (2003). Cyclooxygenase-2 expression in squamous dysplasia and squamous cell carcinoma of the esophagus. Cancer Lett 198, 193-201.

Zhu, Y., Saunders, M. A, Yeh, H., Deng, W. G., and Wu, K. K. (2002). Dynamic regulation of cyclooxygenase-2 promoter activity by isoforms of CCAAT/enhancer-binding proteins. J Biol Chem 277, 6923-6928.

Zhuang, Z. H., Wang, L. D., Tsao, S. W., Cheung, L. M., Feng, H. C., Yang, T., Qin, Y. R., Wang, C. D., Chen, Z. Z., and Liu, B. (2003). [Cyclooxygenase-2 expression in esophageal cancer cells and induction by mitomycin C]. Zhonghua Nei Ke Za Zhi 42, 701-704.

Zimmermann, K. C., Sarbia, M., Weber, A A, Borchard, F., Gabbert, H. E., and Schror, K. (1999). Cyclooxygenase-2 expression in human esophageal carcinoma. Cancer Res 59, 198-204.

---

The invention claimed is:

1. A method for identifying inhibitors of prostaglandin-endoperoxide H synthase-2 (PGHS-2) transactivation activity, the method comprising:
 a) contacting a nucleic acid probe comprising at least one region of a PGHS-2 promoter with PGHS-2 protein in the presence and absence of a test compound; and
 b) determining the level of binding of PGHS-2 protein to the probe;
 wherein the at least one region of the PGHS-2 promoter is selected from the group consisting of a c/EBP site, a CRE site and a NF-kB site, and
 wherein a decrease in amount of protein bound in the presence of said test compound compared to amount of protein bound in the absence of said test compound indicates that the compound is an inhibitor of PGHS-2 transactivation activity.

2. The method of claim 1, wherein the level of binding of PGHS-2 protein to the probe is determined by a DNA-protein binding assay.

3. The method of claim 2, wherein said DNA-protein binding assay is a chromatin immunoprecipitation assay.

4. The method of claim 2, wherein said DNA-binding assay is an electrophoretic mobility shift assay.

5. The method of claim 1, wherein said probe is labeled.

6. The method of claim 5, wherein said probe is biotinylated.

7. A method for identifying inhibitors of prostaglandin-endoperoxide H synthase-2 (PGHS-2) transactivation activity in a cell, wherein said cell constitutively produces PGHS-2, wherein said cell is transfected with a first nucleic acid molecule comprising a region of a PGHS-2 promoter and a second nucleic acid molecule encoding a reporter molecule, wherein the first nucleic acid molecule is operably linked to the second nucleic acid molecule to regulate the transcription of the reporter molecule with the PGHS-2 promoter, and wherein said region of the PGHS-2 promoter is selected from the group consisting of a c/EBP site, a CRE site and a NF-kB site, the method comprising:
 a) exposing said cell to a test compound;
 b) isolating a nuclear extract from said cell; and
 c) comparing the level of reporter molecule in said extract with the level of reporter molecule in a nuclear extract from unexposed cells,
 wherein a decrease in the level of reporter molecule is indicative of inhibition of PGHS-2 transactivation activity.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 1
ggattgggcc ggttcagtgg                                                     20

<210> SEQ ID NO 2
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 2
ggtctaccct ccaatcgcca c                                                   21

<210> SEQ ID NO 3
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 3
ctgttgaaag caacttagct                                                     20

<210> SEQ ID NO 4
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 4
agactgaaaa ccaagcccat                                                     20
```